United States Patent
Lin et al.

(10) Patent No.: US 10,150,351 B2
(45) Date of Patent: Dec. 11, 2018

(54) MACHINE LEARNING FOR OLFACTORY MOOD ALTERATION

(71) Applicant: LP-RESEARCH INC., Tokyo (JP)

(72) Inventors: Zhuohua Lin, Tokyo (JP); Klaus Petersen, Tokyo (JP); Tobias Schlüter, Tokyo (JP); Robert Shiurba, Miyashiro-machi (JP); Huei Ee Yap, Tokyo (JP)

(73) Assignee: LP-Research Inc., Tokyo (JP)

( * ) Notice: Subject to any disclaimer, the term of this patent is extended or adjusted under 35 U.S.C. 154(b) by 0 days.

(21) Appl. No.: 15/427,596

(22) Filed: Feb. 8, 2017

(65) Prior Publication Data

US 2018/0225551 A1   Aug. 9, 2018

(51) Int. Cl.
*B60H 3/00* (2006.01)
*G06K 9/00* (2006.01)
*A61L 9/12* (2006.01)

(52) U.S. Cl.
CPC ............ *B60H 3/0035* (2013.01); *A61L 9/122* (2013.01); *G06K 9/00845* (2013.01)

(58) Field of Classification Search
USPC ............... 180/272; 340/441, 576; 348/77; 352/85; 382/104, 118; 463/16; 700/94; 701/1, 36, 48; 705/14.19, 14.42; 713/186
See application file for complete search history.

(56) References Cited

U.S. PATENT DOCUMENTS

| | | | |
|---|---|---|---|
| 5,574,641 A | 11/1996 | Kawakami et al. | |
| 6,810,309 B2 * | 10/2004 | Sadler | B60R 25/04 701/1 |
| 7,431,120 B2 | 10/2008 | Pollehn et al. | |
| 7,463,157 B2 * | 12/2008 | Victor | A61B 5/11 180/272 |

(Continued)

FOREIGN PATENT DOCUMENTS

| | | |
|---|---|---|
| EP | 1291226 A2 | 3/2003 |
| JP | 2007265377 A | 10/2007 |

(Continued)

OTHER PUBLICATIONS

Lee, W. G., et al., "Intelligent assistance apparatus and method for entertainment of driver," English Translation of Korean Patent KR101305129 B1, Sep. 12, 2013.*

(Continued)

*Primary Examiner* — Xuemei G Chen
(74) *Attorney, Agent, or Firm* — Erise IP, P.A.

(57) ABSTRACT

System, method and media for altering the mood of an occupant (such as a driver) of a vehicle. Reckless operation of motor vehicles by emotionally disturbed drivers is a major cause of traffic accidents just like alcohol, drug, and cell phone use. Emotional states such as annoyance, anger, anxiety, depression, and feeling hurried can significantly impair awareness by slowing observation and reaction times. Scents, both pleasant and unpleasant, have major effects on mood and sense of well-being. Accordingly, embodiments of the invention provide for an adaptive system which can detect a driver's mood, disperse an appropriate scent to improve the mood if it is unsafe, and learn the impact of scents on different users to effectively improve their moods.

20 Claims, 4 Drawing Sheets

(56) References Cited

U.S. PATENT DOCUMENTS

| | | | |
|---|---|---|---|
| 7,821,382 B2 | 10/2010 | Kameyama | |
| 8,108,083 B2* | 1/2012 | Kameyama | G01C 21/3641 180/272 |
| 8,140,344 B2* | 3/2012 | Kameyama | B60H 1/00742 382/104 |
| 8,930,085 B2* | 1/2015 | Takeuchi | B60W 50/085 340/441 |
| 9,135,803 B1* | 9/2015 | Fields | B60K 28/066 |
| 2003/0199295 A1* | 10/2003 | Vancura | G07F 17/32 463/16 |
| 2004/0007787 A1 | 1/2004 | Kvietok et al. | |
| 2006/0283652 A1 | 12/2006 | Yanai et al. | |
| 2008/0119994 A1* | 5/2008 | Kameyama | B60W 40/08 701/48 |
| 2010/0134302 A1* | 6/2010 | Ahn | A61B 5/165 340/576 |
| 2010/0309434 A1* | 12/2010 | Van Schijndel | A61L 9/035 352/85 |
| 2010/0332842 A1* | 12/2010 | Kalaboukis | G06F 17/30867 713/186 |
| 2011/0190913 A1* | 8/2011 | Van De Sluis | A63J 17/00 700/94 |
| 2014/0316881 A1* | 10/2014 | Movellan | G06K 9/00315 705/14.42 |
| 2015/0053066 A1 | 2/2015 | Hampiholi et al. | |
| 2015/0178624 A1* | 6/2015 | Chee | G06K 9/6217 706/11 |
| 2015/0186714 A1* | 7/2015 | Ren | G06K 9/00369 348/77 |
| 2015/0186912 A1* | 7/2015 | el Kaliouby | G06Q 30/0217 705/14.19 |
| 2015/0206000 A1* | 7/2015 | el Kaliouby | G06K 9/00315 382/118 |
| 2015/0254955 A1 | 9/2015 | Fields et al. | |
| 2016/0001781 A1* | 1/2016 | Fung | G06F 19/345 701/36 |
| 2016/0046298 A1* | 2/2016 | DeRuyck | B60W 40/09 340/576 |
| 2016/0089954 A1* | 3/2016 | Rojas Villanueva | G01C 21/3484 701/36 |
| 2017/0011258 A1* | 1/2017 | Pitre | A61B 5/7264 |
| 2017/0028876 A1* | 2/2017 | Yamada | B60N 2/012 |
| 2017/0109571 A1* | 4/2017 | McDuff | G06K 9/00302 |
| 2017/0369168 A1* | 12/2017 | Hwang | B64D 1/18 |
| 2018/0001899 A1* | 1/2018 | Shenoy | B60W 40/09 |
| 2018/0063064 A1* | 3/2018 | Borse | H04L 51/32 |

FOREIGN PATENT DOCUMENTS

| | | |
|---|---|---|
| JP | 2014021783 A | 2/2014 |
| KR | 101998026948 A | 7/1998 |
| KR | 101305129 B1 | 9/2013 |
| KR | 101536348 B1 | 7/2015 |
| WO | 2014085302 A1 | 6/2014 |

OTHER PUBLICATIONS

PCT/US2017/016949 International Search Report and Written Opinion dated Oct. 20, 2017.

* cited by examiner

MACHINE LEARNING FOR OLFACTORY MOOD ALTERATION

BACKGROUND

1. Field

Embodiments of the invention generally relate to vehicular safety and, more particularly, to techniques for reducing unsafe emotional states in vehicle operators through the use of scent to alter an emotional state unsafe for driving to a safer one.

2. Related Art

Reckless operation of motor vehicles by emotionally disturbed drivers is a major cause of traffic accidents just like alcohol, drug, and cell phone use. Emotional states such as annoyance, anger, anxiety, depression, and feeling hurried can significantly impair awareness by slowing observation and reaction times. The ability to determine and foresee what nearby drivers are doing and might do is critical to recognizing and reacting to road hazards such as debris and abrupt slowing of the traffic ahead. Other dangerous maneuvers may include sudden changes in traffic lanes and driving on the freeway shoulder or center divider.

The human sense of smell has a direct link to the limbic system, an evolutionarily ancient neural network in the brain concerned with basic emotions and instincts. Such emotions include pleasure, anger, and fear. Nasal receptors for volatilized chemical compounds in the environment known as scents generate signals in neurons of the olfactory cortex. The resultant signals travel through the limbic system to the cerebral cortex, where they are recognized and identified.

Scents, both pleasant and unpleasant, have major effects on mood and sense of well-being. Complexity arises, because these effects can be strongly influenced by one's previous experiences and expectations. Nevertheless, scents are potential mood-altering tools in situations where negative aspects of emotions may contribute to reckless behavior that results in physical injury. Examples include road rage, drowsiness, and panic associated with operation of motorized vehicles. However, reactions to scents vary from person to person and, for the same person, over time. Accordingly, there is a need for an adaptive system which can detect a driver's mood, disperse an appropriate scent to improve the mood if it is unsafe, and learn the impact of scents on different users to effectively improve their moods.

SUMMARY

Embodiments of the invention address the above-described by providing for a system which uses machine learning algorithms to close the loop by learning to classify a driver's mood based on dispersed scents, and learning which scents to disperse based on the driver's classified mood. In particular, in a first embodiment, the invention include a system for altering a mood of an occupant of a vehicle, comprising one or more cameras located in the vehicle and configured to capture facial imagery of the occupant of the vehicle, one or more scent dispersion units, each scent dispersion unit configured to disperse a scent perceptible to the occupant of the vehicle, a processor, and one or more non-transitory computer storage media storing one or more occupant profiles, wherein each occupant profile comprises mood classification information and mood actuation information and computer-executable instructions that, when executed by the processor, perform a method of altering the mood of the occupant of the vehicle, the method comprising the steps of determining an identity of the occupant of the vehicle, loading an occupant profile for the occupant of the vehicle from the one or more occupant profiles, obtaining initial facial imagery of the occupant from the one or more cameras, identifying, based at least in part on the initial facial imagery of the occupant and the mood classification information, a current mood for the occupant, determining, from the mood actuation information, a mood actuation to change the current mood to a desired mood, dispersing one or more scents associated with the mood actuation, obtaining updated facial imagery of the occupant from the one or more cameras, identifying, based at least in part on the updated facial imagery of the occupant and the mood classification information, an updated mood for the occupant, and updating the mood actuation information based on the updated mood for the occupant and the dispersed one or more scents.

In a second embodiment, the invention includes a method of altering a mood of an occupant of a vehicle, comprising the steps of determining an identity of the occupant of the vehicle, obtaining initial facial imagery of the occupant from one or more cameras in the vehicle, identifying, based at least in part on the initial facial imagery of the occupant and mood classification information for the occupant, a current mood for the occupant, determining, from mood actuation information for the occupant, a mood actuation to change the current mood to a desired mood, dispersing one or more scents associated with the mood actuation, obtaining updated facial imagery of the occupant from the one or more cameras, identifying, based at least in part on the updated facial imagery of the occupant and the mood classification information, an updated mood for the occupant, and updating the mood classification information based on the updated facial imagery and the mood actuation.

In a third embodiment, the invention includes One or more computer storage media storing computer-executable instructions that, when executed by a processor, perform a method of altering a mood of an occupant of a vehicle, the method comprising the steps of determining an identity of the occupant of the vehicle, obtaining initial facial imagery of the occupant from one or more cameras in the vehicle, obtaining physiological data for the occupant from one or more physiological sensors in the vehicle, identifying, based at least in part on the initial facial imagery of the occupant, the physiological data for the occupant, and mood classification information for the occupant, a current mood for the occupant, determining, from mood actuation information for the occupant, a mood actuation to change the current mood to a desired mood, dispersing one or more scents associated with the mood actuation, obtaining updated facial imagery of the occupant from the one or more cameras, identifying, based at least in part on the updated facial imagery of the occupant and the mood classification information, an updated mood for the occupant, updating the mood actuation information based on the updated mood for the occupant and the dispersed one or more scents, and updating the mood classification information based on the updated facial imagery and the mood actuation.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

The drawing figures do not limit the invention to the specific embodiments disclosed and described herein. The drawings are not necessarily to scale, emphasis instead being placed upon clearly illustrating the principles of the invention.

DETAILED DESCRIPTION

At a high level, embodiments of the invention determine when a driver or other occupant of a vehicle is in an unsafe mood, determine a scent likely to improve their mood, and disperse the scent into the vehicle. However, different drivers will display their moods differently and react to scents differently. Accordingly, machine learning is used to refine the recognition of safe and unsafe moods in individual drivers based on supplementary sensors and driving performance data. Similarly, machine learning is used to determine scents that can change a particular unsafe mood into a safer one. Additionally, the mood recognition model and the mood actuation (alteration) model back propagate into each other such that, for example, an expected mood resulting from a given scent can be used to refine the recognition of that mood. Similarly, recognized moods after scents are dispersed can be used to refine the expected impacts of that scent.

The subject matter of embodiments of the invention is described in detail below to meet statutory requirements; however, the description itself is not intended to limit the scope of claims. Rather, the claimed subject matter might be embodied in other ways to include different steps or combinations of steps similar to the ones described in this document, in conjunction with other present or future technologies. Minor variations from the description below will be obvious to one skilled in the art, and are intended to be captured within the scope of the claimed invention. Terms should not be interpreted as implying any particular ordering of various steps described unless the order of individual steps is explicitly described.

The following detailed description of embodiments of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of embodiments of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate reference to "one embodiment" "an embodiment", or "embodiments" in this description do not necessarily refer to the same embodiment and are also not mutually exclusive unless so stated and/or except as will be readily apparent to those skilled in the art from the description. For example, a feature, structure, or act described in one embodiment may also be included in other embodiments, but is not necessarily included. Thus, the technology can include a variety of combinations and/or integrations of the embodiments described herein.

Figure 1:
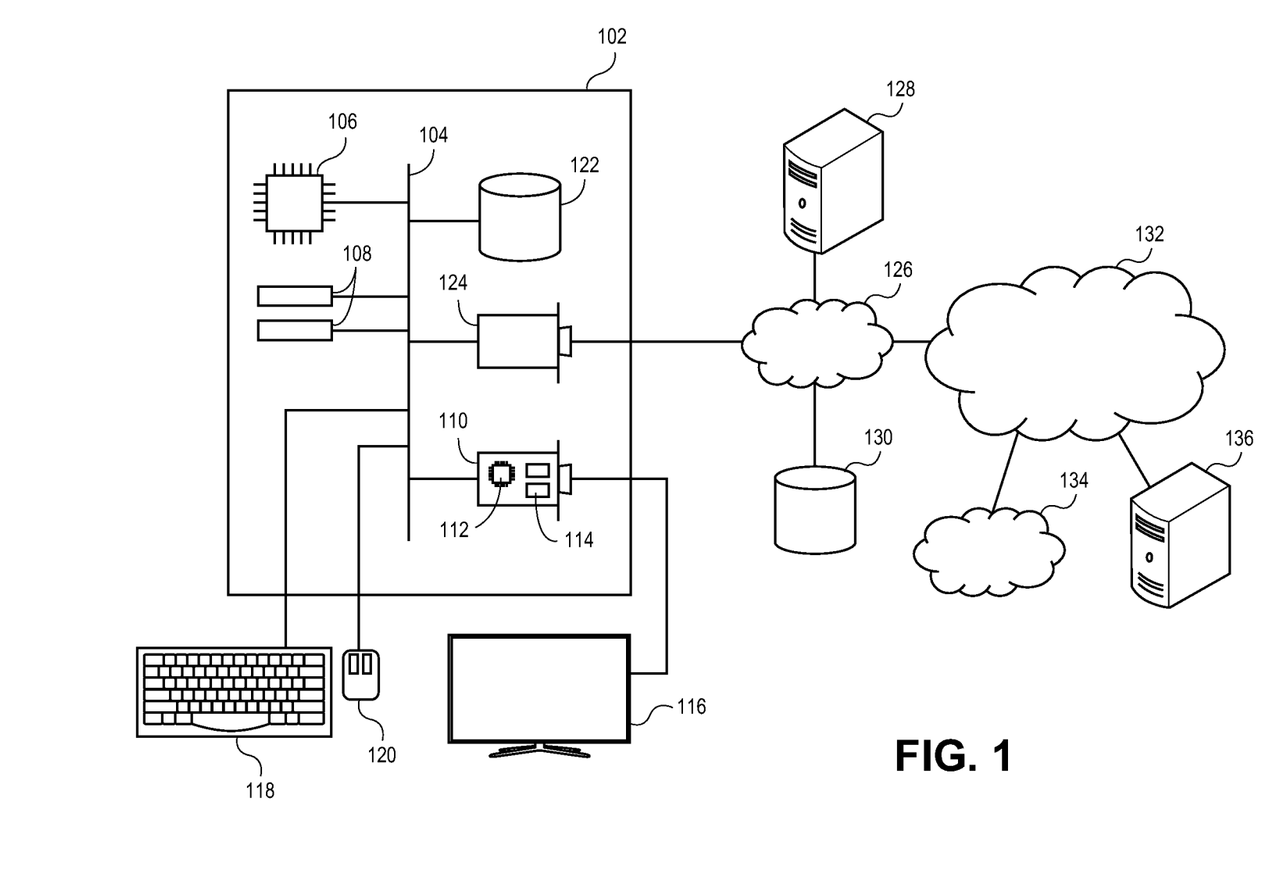
FIG. 1 depicts an exemplary hardware platform for certain embodiments of the invention.

Turning first to FIG. 1, an exemplary hardware platform for certain embodiments of the invention is depicted. Computer 102 can be a desktop computer, a laptop computer, a server computer, a mobile device such as a smartphone or tablet, or any other form factor of general- or special-purpose computing device. Depicted with computer 102 are several components, for illustrative purposes. In some embodiments, certain components may be arranged differently or absent. Additional components may also be present. Included in computer 102 is system bus 104, whereby other components of computer 102 can communicate with each other. In certain embodiments, there may be multiple busses or components may communicate with each other directly. Connected to system bus 104 is central processing unit (CPU) 106. Also attached to system bus 104 are one or more random-access memory (RAM) modules. Also attached to system bus 104 is graphics card 110. In some embodiments, graphics card 104 may not be a physically separate card, but rather may be integrated into the motherboard or the CPU 106. In some embodiments, graphics card 110 has a separate graphics-processing unit (GPU) 112, which can be used for graphics processing or for general purpose computing (GPGPU). Also on graphics card 110 is GPU memory 114. Connected (directly or indirectly) to graphics card 110 is display 116 for user interaction. In some embodiments no display is present, while in others it is integrated into computer 102. Similarly, peripherals such as keyboard 118 and mouse 120 are connected to system bus 104. Like display 116, these peripherals may be integrated into computer 102 or absent. Also connected to system bus 104 is local storage 122, which may be any form of computer-readable media, and may be internally installed in computer 102 or externally and removeably attached.

Computer-readable media include both volatile and non-volatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-useable instructions, data structures, program modules, and other data representations.

Finally, network interface card (NIC) 124 is also attached to system bus 104 and allows computer 102 to communicate over a network such as network 126. NIC 124 can be any form of network interface known in the art, such as Ethernet, ATM, fiber, Bluetooth, or Wi-Fi (i.e., the IEEE 802.11 family of standards). NIC 124 connects computer 102 to local network 126, which may also include one or more other computers, such as computer 128, and network storage, such as data store 130. Generally, a data store such as data store 130 may be any repository from which information can be stored and retrieved as needed. Examples of data stores include relational or object oriented databases, spreadsheets, file systems, flat files, directory services such as LDAP and Active Directory, or email storage systems. A data store may be accessible via a complex API (such as, for example, Structured Query Language), a simple API providing only read, write and seek operations, or any level of complexity in between. Some data stores may additionally provide management functions for data sets stored therein such as backup or versioning. Data stores can be local to a single computer such as computer 128, accessible on a local network such as local network 126, or remotely accessible over Internet 132. Local network 126 is in turn connected to Internet 132, which connects many networks such as local network 126, remote network 134 or directly attached computers such as computer 136. In some embodiments, computer 102 can itself be directly connected to Internet 132.

Figure 2:
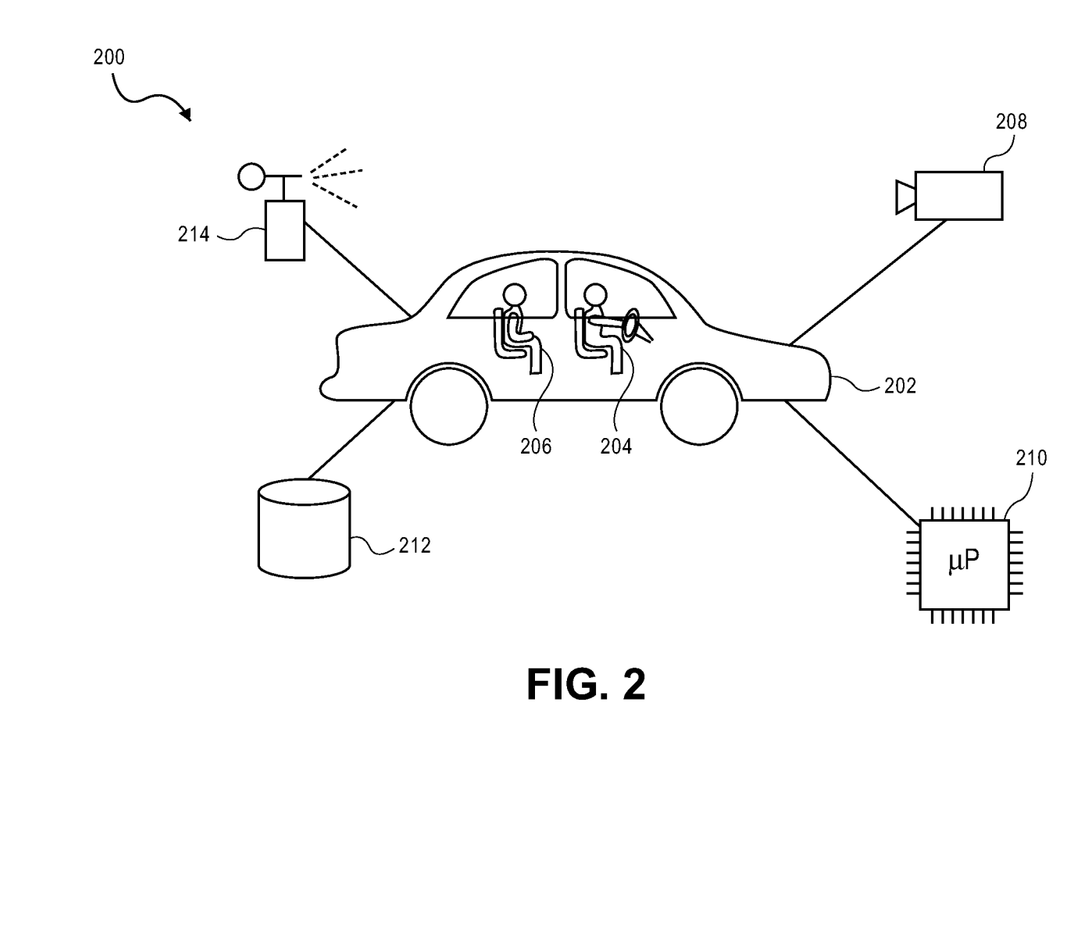
FIG. 2 depicts an exemplary environment suitable for deploying certain embodiments of the invention.

Turning now to FIG. 2, an exemplary environment suitable for deploying certain embodiments of the invention is depicted and referred to generally by reference numeral 200. Vehicle 202 is one example of a platform suitable for embodiments of the invention. For example, vehicle 200 may be a car, truck, sport utility vehicle, or any other form of transportation. In some embodiments, vehicle 200 may instead be an airplane, train, boat, or other method of transportation. Broadly speaking, any form of public or private conveyance is contemplated as being within the scope of the invention. Vehicle 202 may be a conventional (driver-operated) vehicle, an autonomous (self-driving) vehicle, or a hybrid of the two (for example, a partially autonomous vehicle requiring a driver presence but only limited activity or supervision).

Vehicle 202 has one or more occupants such as driver 204 and passenger 206. In some embodiments, vehicle 202 is autonomous and has no driver 204. In some embodiments, vehicle 202 has a plurality of passengers 206. In other embodiments, vehicle 202 has no passengers 206. Broadly speaking, embodiments of the invention can be used whenever vehicle 202 has at least one occupant of any type.

Also present in vehicle 202 are one or more cameras 208 positioned so as to capture facial imagery of driver 204 and/or passenger 206. In some embodiments, cameras 208 capture visible-spectrum light. In other embodiments, cameras 208 capture infrared light instead of (or in addition to) visible light. In some embodiments, cameras 208 may be equipped with a visible or infrared light source (for example, one or more light-emitting diodes of the appropriate frequency or frequencies). In some embodiments, cameras 208 are fixedly oriented; in other embodiments, cameras 208 can be automatically or manually re-aimed. For example, cameras 208 may be mounted via pan/tilt/zoom mounts so as to continuously capture imagery of driver 204 and/or passenger 206 regardless of their movements. In some embodiments, only a single camera 208 is present, but it is mounted via a pan/tilt/zoom mount so as to selectively capture imagery of different occupants. In some embodiments, additional sensors are also present. For example, cameras 208 may be supplemented by a heart-rate sensor integrated into a steering wheel of vehicle 202. Other sensors (e.g., accelerometers for detecting occupant motion) for determining the mood or behavior of the occupants of vehicle 202 are also contemplated as being within the scope of the invention.

Cameras 208 are communicatively coupled to processor 210 and/or data store 212. Processor 210 may further be communicatively coupled to any of the components described above with respect to FIG. 1. For example, a touchscreen display for processor 201 may be integrated into the dashboard of vehicle 202. In some embodiments, processor 210 may be connected to the CAN (Controller Area Network) or VAN (Vehicle Area Network) bus for vehicle 202, and can obtain driving performance data therefrom to assist in mood classification for driver 204. In some embodiments, cameras 208 transmit imagery to processor 210. In other embodiments, Cameras 208 store imagery in data store 212 for later processing by processor 210. Data store 212 may also store configuration data for the system and one or more occupant mood profiles, as discussed in greater detail below.

Vehicle 202 further includes one or more scent dispersion units 214. Broadly speaking, scent dispersion unit is any device for dispersing a scent perceptible (consciously or unconsciously) to an occupant of vehicle 202. For example, a scent dispersion unit 214 may include one or more electronically controlled atomizers connected to respective scent reservoirs. In some embodiments, a scent dispersion unit 214 includes a scent reservoir attached to a scent dispersion nozzle. Integrated into the scent dispersion nozzle is a fan that propels air from the scent reservoir into the scent dispersion nozzle and from there into the interior of the car. The speed of the fan (and thus the amount of scent dispersed) may be controlled via a control circuit that sends a variable pulse-width modulated voltage to the fan motor. In some embodiments, a scent dispersion unit 214 includes a plurality of scents, each with a respective reservoir and nozzle. These nozzles may be places in close proximity for immediate mixing of dispersed scents.

Scent dispersion units may disperse the scent into the entirety of vehicle 202, into only the vicinity of a single occupant, or directly to a single occupant (using, for example, a mask or nose tube). Scent dispersion units 214 are under the control of processor 210 and may also be manually operated by the occupants of vehicle 202. As discussed below, each scent dispersion units may be capable of dispersing a single scent, or a wide variety of scents or combinations of scents. Broadly speaking, any scent is contemplated as being with the scope of the inventions. For example, one vehicle 202 might include scent reservoirs for rose, lemon, lavender, and sandalwood. Another vehicle 202 might include scent reservoirs for cinnamon, peppermint, and leather.

In some embodiments, a scent dispersion unit 214 is included for each occupant of vehicle 202, such as driver 204 and passenger 206. In other embodiments, a scent dispersion unit 214 is included only for driver 204. In those embodiments where scent dispersion units are included for multiple occupants, the respective scent dispersion units may be located in close proximity to the locations of the respective occupants so as to localize the dispersed scent. For example, a scent dispersion unit 214 for a driver may be located under the steering wheel, in the driver's side door, under the driver's seat, or in any other location near the driver. Scent dispersion units 214 may also be distributed throughout vehicle 202, with nozzles for different scents located in different locations. In some embodiments, one or more fans or other blowers are additionally included to more effectively circulate the dispersed scents throughout vehicle 202.

Figure 3:
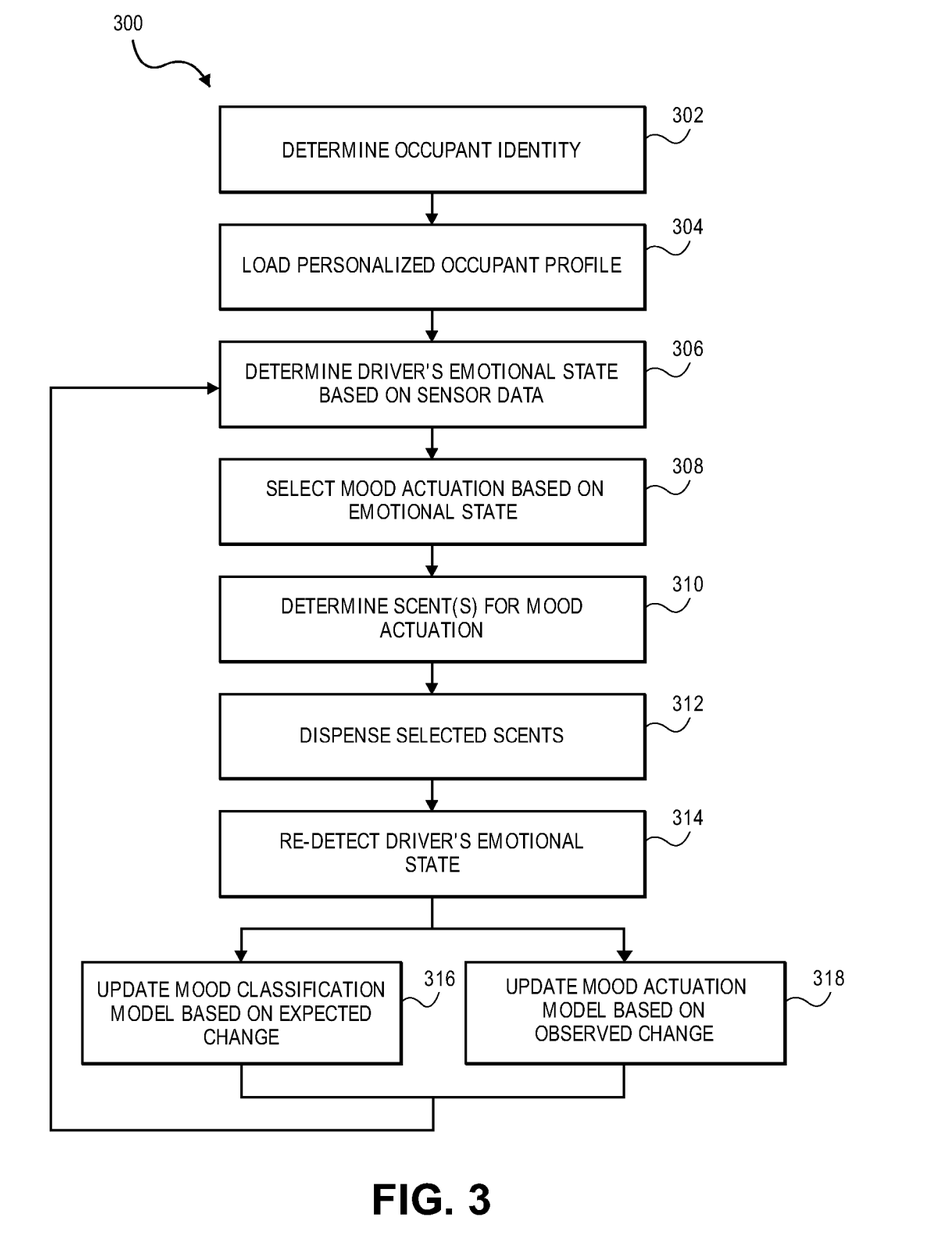
FIG. 3 depicts a flowchart illustrating the operation of a method in accordance with embodiments of the invention.

Turning now to FIG. 3, a flowchart depicting a method in accordance with embodiments of the present invention is depicted and referred to generally by reference numeral 300. Initially, at a step 302, camera 208 captures an image of an occupant of vehicle 202. Based on that image, the system can determine an identity of the occupant. In some embodiments, the system uses facial recognition on the captured image to identify the occupant. In other embodiments, another method not requiring a preliminary image capture is used. For example, the driver of a vehicle may be recognized via a personalized ignition key or key fob. Other methods of recognizing occupants of the vehicle are also contemplated. For example, the system may communicate with a smartphone of the occupant to determine their identity. In some embodiments, multiple vehicle occupants are recognized at this step. Broadly, the system can communicate with any item such as the above-described key fob or smartphone (collectively, "transponders") in order to identify the occupant or occupants of the vehicle.

Next, at a step 304, the system loads a personalized occupant profile for the recognized occupant from data store 212. Broadly speaking, an occupant profile may include mood classification information for the occupant and/or mood actuation information for the occupant. Mood classification information allows the system to determine a mood for the occupant based on sensor information (e.g., the imagery from cameras 208 and/or the other sensors), past mood information, feedback from actuated scent dispersion units 214, and any other inputs. Broadly speaking, any information useful to determine an occupant's mood can be a part of that occupants personalized occupant profile. Mood actuation information includes information on how particular scents or combinations of scents can change an occupant's mood in particular ways, as discussed in greater details below. Both the mood classification information and the mood actuation information for a particular occupant can evolve over time, as further discussed below.

Processing can then proceed to a step 306, where the occupant's emotional state can be determined based on data from camera 208 and/or any supplemental sensors. In some embodiments, a facial mood model is used to determine a mood for the occupant based on their facial expression. For example, a first machine learning model might detect a face in the model, extract the geometrical and biological features of the face (as described, for example, by the Facial Action Coding System (FACS) or the Emotional FACS), and then pass the action units coded by the first machine learning model to an occupant-specific mood classifier which determines a mood for the occupant based on the received action units. Thus, for a given frame of video imagery, the first machine-learning model might determine that the facial actions include 4 (Brow Lowered), 7 (Lids Tightened), and 23 (Lips Tightened). The mood classifier might then determine (based on the occupant profile) that that set of actions corresponds to the mood "angry" for the current occupant. One of skill in the art will appreciate that a different occupant might have a different set of facial actions indicating an "angry" mood, while the described set of facial actions might indicate a different mood, or no mood.

In some embodiments, the data from any supplementary sensors is also used when determining the occupant's mood. For example, given set of facial actions in combination with an elevated heart rate might indicate a different mood than the same set of facial actions with a baseline heart rate. In other embodiments, the data from the supplementary sensors is used to determine the intensity for a determined mood. For example, if the face indicates an "angry" mood, then an elevated heart rate might indicate that the occupant is very angry, while a baseline heart rate might indicate that the vehicle occupant is slightly angry. In some embodiments, data from the vehicle's onboard sensors is also used in determining the occupant's mood. For example, a sudden acceleration might result in an elevated heart rate in the vehicle occupant. When determining the occupant's mood, an elevated heart rate in combination with a sudden acceleration might indicate a mood of "agitated" rather than "angry."

Once the occupant's mood has been determined, processing can proceed to a step 308, where a mood actuation is selected. Broadly speaking, a mood actuation comprises a detected mood and a target mood. For example, a first mood actuation might be based on the premise that a happy driver is a better driver than an angry driver. As such, if a driver is determined to be angry, than a mood actuation that transitions the driver from an angry mood to a happy mood may be selected. A second mood actuation may be based on the premise may be that a calm driver is a better driver than an excited driver. Accordingly, if the driver is determined to be ecstatic (or otherwise overly excited), than a mood actuation that calms an excited driver may be selected. In some embodiments, mood actuations are the same for all occupants of the vehicle. In other embodiments, different mood actuations are used for drivers and passengers. In still other embodiments, different mood actuations may be used for each vehicle occupant, as stored in the occupant profile. Certain detected moods may not have an associated mood actuation. For example, if the driver is determined to be calm and happy, no actuation may be needed. Any mood actuation is contemplated as being in the scope of the invention.

Next, a step 310, one or more scents are determined for the selected mood actuation. As described above, different occupants may react to different scents differently, and the same occupant may react differently to the same scent when in different moods. Furthermore, an occupant's reaction to a given scent may change over time. For example, if an occupant associates a given scent with another person, then the occupant's reaction to the scent may vary depending on their current relationship with that person. As such, a mood actuation machine-learning model is used to predict the impact of a particular scent on a given occupant.

In order to train the mood actuation machine-learning model, a random scent may be selected for dispersal to determine its impact on the occupant's mood. In some embodiments, the system may undergo a training period when scents are selected at random until their effectiveness in various mood actuations can be determined. In other embodiments, the system begins with baseline effects for each scent, which are then customized for each occupant based on their observed effects.

The mood actuation associated with a given scent or combination of scents can be determined based on the occupant's mood or mood change after exposure to the scent or combination of scents. In some embodiments, the mood actuation associated with a scent is dependent on the occupant's mood prior to exposure to the scent as well as their mood after exposure to the scent. For some scents, the associated mood actuation may be the intensification or moderation of a preexisting mood of the occupant rather than an alteration from one mood to another mood. As discussed elsewhere, mood actuations associated with various scents are continuously updated, as an occupant's response to a scent may vary over time.

Processing can then proceed to step 312, where the selected scent or combination of scents is dispersed. In some embodiments, as discussed above, the same scents are dispersed for the entire vehicle. In other embodiments, scent dispersal may be localized to a single occupant or subset of occupants of the vehicle. As described above, scents may be dispersed via aerosolization of essential oils or other infused liquids. Alternatively, fans or blowers might be used in conjunction with reservoirs of volatile fluids to disperse scents. Any method of introducing a scent to the perception of an occupant, whether the scent is real or only perceived by the occupant, is contemplated as being within the scope of the present invention.

Next, at step 314, the system re-determines the occupant's mood after the scent has been dispersed. In some embodiments, the occupant's mood is continually evaluated. In other embodiments, the occupant's mood is determined only upon certain triggers, such as a scent being dispersed. In some embodiments, the occupant's mood may be continuously re-evaluated after a scent is dispersed until a mood change is detected or enough time has elapsed to determine that the scent has had no impact upon the occupant's mood. In other embodiments, the occupant's mood is monitored continuously and, if a change to a mood with an associated actuation is detected, the appropriate scent is determined and dispersed in steps 310 and 312.

Processing can then proceed to step 316 and/or 318. At step 316, the mood classification model is updated based on the expected results of the mood actuation and the observed change in the occupant's mood. For example, if a particular mood actuation is expected to change an occupant's mood to "happy," and a change in mood does occur after the mood actuation, then the mood classification model may weight the occupant's post-actuation facial expression more strongly as "happy." Similarly, if a mood actuation is expected to calm an occupant, and supplementary sensors detect a reduction in pulse, blood pressure, skin conductivity, or some other stress indicator, then the occupant's post-actuation expression may be re-weighted towards "calm." The precise process of re-weighting the mood classification model will depend on the precise model used, as discussed below.

At step 318, the mood actuation model is updated based on the observed change in the occupant's mood. For example, if a particular mood actuation is expected to change an occupant's mood towards "happy" and the observed mood is instead "sad," then that actuation would be de-weighted. Similarly, as described above, if a mood actuation is expected to calm an occupant, and the supplementary sensors detect increased stress levels, then the mood actuation may be de-weighted accordingly. Mood actuations that behave as expected can be weighted more heavily or left at their previous weights. As with the mood classification model, the process of re-weighting mood actuation model will depend on the precise model used.

In some embodiments, both steps 316 and 318 may be performed after scents are dispersed to implement a mood actuation. In other embodiments, only one is performed. In still other embodiments, step 316 is performed if the mood actuation produces an expected result and step 318 is performed if the mood actuation does not perform the expected result. In still other embodiments, step 316 is performed only if the observed mood after the mood actuation shares sufficient facial features with the mood expected to result from the actuation. In yet other embodiments, one of step 316 and step 318 is selected to be performed based on how closely the observed mood after the mood actuation matches the expected mood after the actuation. In some embodiments, an initial training or calibration procedure can be used to train mood classification model and/or mood actuation model rather than an ongoing learning process. In other embodiments, the initial training or calibration process can be used to determine an initial mood classification model or mood actuation model, which is then refined by the ongoing learning process. Broadly, performing any combination of steps 316 and 318, based on any criteria, is contemplated as being within the scope of the invention. Once steps 316 and/or 318 have been performed, processing can return to step 306, where the occupant's mood continues to be monitored for potential additional mood actuations.

Figure 4:
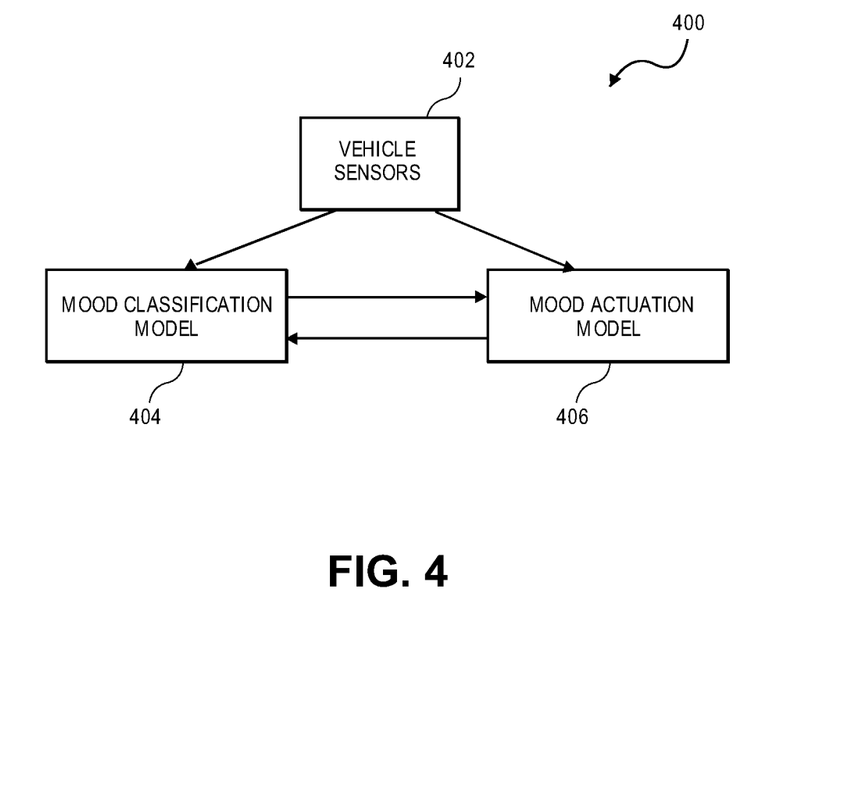
FIG. 4 depicts a block diagram depicting certain high-level components of the invention and their interrelation.

Turning now to FIG. 4, a block diagram depicting certain high-level components of the invention and their interrelation is depicted and referred to generally by reference numeral 400. Depicted are vehicle sensors 402, mood classification model 404, and mood actuation model 406. As described above, vehicle sensors 402 may include cameras 208 or other biometric sensors as well as physiological sensors (or Body Area Network (BAN) sensors) for one or more vehicle occupants. Vehicle sensors 402 may also include onboard automotive sensors connected to the CAN or VAN bus for the vehicle that can provide insight into the occupant's mood. For example, if the driver of the vehicle is accelerating and braking hard, honking the horn, or steering abruptly, it may be an indication that the driver's mood is angry. If the driver executes a panic stop (as indicated by the vehicle's anti-lock brakes engaging), it may indicate that an upsetting event has just occurred. Other vehicular sensors or telemetry may also provide insight into vehicular events that may impact the mood of vehicular occupants.

Data from vehicular sensors 402 is passed to mood classification model 404 and mood actuation model 406. Mood classification model may be any variety of machine-learning system now known or later developed in the art. For example, a support vector machine (SVM), convolutional neural network (CNN), or hidden Markov model (HMM) may be used to determine an occupant's mood from the data provided by vehicle sensors 402. In some embodiments, data from mood actuation model 406 is further used in evaluating an occupant's mood. For example, if a mood actuation causes a scent to be released that is expected to change an occupant's mood to "happy," this information can be passed to mood classification model 402 to better distinguish between related facial expressions (such as, for example, a grin and a grimace). In some embodiments, the mood classification model may include a preliminary facial action recognizer programmed to take visual imagery from camera(s) 208, normalize it, and translate it into coded facial actions which are used (together with, in some embodiments, other data from vehicle sensors 402) to determine the occupant's mood.

In some embodiments, a baseline training model is used as an initial model for all occupants. For example, generic FACS classification data may be used to provide a mood classification for a new occupant profile until the data can be refined via back propagation from other sensors and mood actuation model 406. In other embodiments, an occupant can provide an initial set of training data either by providing imagery in a set of pre-specified moods (happy, tired, etc.) or by specifying the mood for imagery otherwise obtained (either from cameras 208 or from outside sources such as social media). Similarly, data form other sensors can be initially based on generic values or based on values in known situations prior to refinement for a given occupant via back-propagation. For example, if a sensor measures the occupant's pulse to determine stress level, then a rate of 80 beats per minute could be initially considered baseline. Alternatively, the average measured pulse rate over a week for the occupant could be used as the baseline. As the occupant spends more time in the vehicle, additional data can be gathered to refine the mood model for the occupant.

Mood actuation model 406 may be the same type of machine learning model as mood classification model 404 or a different type of machine learning model. In some embodiments, a single machine learning system functions as both mood classification model 404 and mood action model 406. In some embodiments, a mood actuation model includes one or more mood actuations and each mood actuation includes a starting mood, a desired target mood, and a scent to actuate a transition from the starting mood to the desired mood. For example, one mood actuation might be dispersing lavender scent to change an occupant from an "angry" mood to a "calm" mood.

In some embodiments, undesirable starting moods or desirable ending moods may be preconfigured into the system. In other embodiments, driver performance data from vehicle sensors 402 is used in combination with mood classification model 404 to determine moods in which the driver of vehicle 202 drives the best. As with mood classification model 404, an initial generic profile may be provided. For example, lavender may be a scent that is calming to most people and, if the desired mood is "calm," a lavender scent dispersed unless data is gathered showing that it is ineffective for a particular occupant. In other embodiments, an initial training procedure may be undertaken where a variety of scents are dispersed to a new occupant and their effects on the occupant's mood observed.

Many different arrangements of the various components depicted, as well as components not shown, are possible without departing from the scope of the claims below. Embodiments of the invention have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims. Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A system for altering a mood of an occupant of a vehicle, comprising:
   one or more cameras located in the vehicle and configured to capture facial imagery of the occupant of the vehicle;
   one or more scent dispersion units, each scent dispersion unit configured to disperse a scent perceptible to the occupant of the vehicle;
   a processor;
   one or more non-transitory computer storage media storing:
   one or more occupant profiles, wherein each occupant profile comprises mood classification information and mood actuation information; and
   computer-executable instructions that, when executed by the processor, perform a method of altering the mood of the occupant of the vehicle, the method comprising the steps of:
   determining an identity of the occupant of the vehicle;
   loading an occupant profile for the occupant of the vehicle from the one or more occupant profiles;
   obtaining initial facial imagery of the occupant from the one or more cameras;
   identifying, based at least in part on the initial facial imagery of the occupant and the mood classification information, a current mood for the occupant;
   determining, from the mood actuation information, a mood actuation to change the current mood to a desired mood;
   dispersing one or more scents associated with the mood actuation;
   obtaining updated facial imagery of the occupant from the one or more cameras;
   identifying, based at least in part on the updated facial imagery of the occupant and the mood classification information, an updated mood for the occupant; and
   updating the mood actuation information based on the updated mood for the occupant and the dispersed one or more scents through a machine learning model.

2. The system of claim 1, wherein the identity of the occupant is determined by recognizing a face of the occupant in the facial imagery of the occupant.

3. The system of claim 1, wherein the method further comprises the step of updating the mood classification information based on the updated facial imagery and the mood actuation.

4. The system of claim 1, wherein the system further comprises one or more supplementary sensors, and wherein the current mood is determined in part based on data from the supplementary sensors.

5. The system of claim 4, wherein the one or more supplementary sensors include a heart-rate sensor for the occupant.

6. The system of claim 1, wherein the system further includes one or more onboard automotive sensors, and wherein current mood is determined in part based on data from the one or more onboard automotive sensors.

7. The system of claim 1, wherein the current mood indicates that the occupant is angry and the desired mood is a calm mood.

8. The system of claim 1, wherein the current mood indicated that the occupant is distracted and the desired mood is an alert mood.

9. A method of altering a mood of an occupant of a vehicle, comprising the steps of:
   determining an identity of the occupant of the vehicle;
   obtaining initial facial imagery of the occupant from one or more cameras in the vehicle;
   identifying, based at least in part on the initial facial imagery of the occupant and mood classification information for the occupant, a current mood for the occupant;
   determining, from mood actuation information for the occupant, a mood actuation to change the current mood to a desired mood;
   dispersing one or more scents associated with the mood actuation;

obtaining updated facial imagery of the occupant from the one or more cameras;

identifying, based at least in part on the updated facial imagery of the occupant and the mood classification information, an updated mood for the occupant; and updating the mood classification information based on the updated facial imagery and the mood actuation through a machine learning model.

10. The method of claim 9, further comprising the step of updating the mood actuation information based on the updated mood for the occupant and the dispersed one or more scents.

11. The method of claim 9, wherein the identity of the occupant is determined based on a transponder carried by the occupant.

12. The method of claim 9, wherein the current mood is identified based in part on physiological data for the occupant obtained from one or more supplementary sensors in the vehicle.

13. The method of claim 12, wherein the physiological data is heart rate data and wherein the one or more supplementary sensors include a heart-rate sensor.

14. The method of claim 9, wherein the current mood is identified based in part on driving data for the vehicle obtained from one or more onboard vehicular sensors.

15. The method of claim 9, wherein the current mood is excited, and the desired mood is calm.

16. One or more computer storage media storing computer-executable instructions that, when executed by a processor, perform a method of altering a mood of an occupant of a vehicle, the method comprising the steps of:

determining an identity of the occupant of the vehicle;

obtaining initial facial imagery of the occupant from one or more cameras in the vehicle;

obtaining physiological data for the occupant from one or more physiological sensors in the vehicle;

identifying, based at least in part on the initial facial imagery of the occupant, the physiological data for the occupant, and mood classification information for the occupant, a current mood for the occupant;

determining, from mood actuation information for the occupant, a mood actuation to change the current mood to a desired mood;

dispersing one or more scents associated with the mood actuation;

obtaining updated facial imagery of the occupant from the one or more cameras;

identifying, based at least in part on the updated facial imagery of the occupant and the mood classification information, an updated mood for the occupant;

updating the mood actuation information based on the updated mood for the occupant and the dispersed one or more scents through a first machine learning model; and updating the mood classification information based on the updated facial imagery and the mood actuation through a second machine learning model.

17. The media of claim 16, wherein the identity of the occupant is determined using facial recognition on the initial facial imagery of the occupant.

18. The media of claim 16, wherein the method further comprises the step of obtaining driving data from one or more onboard vehicular sensors, and wherein the current mood is determined in part based on the driving data.

19. The media of claim 16, wherein the media further stores a plurality of personalized occupant profiles, each personalized occupant profile comprising mood classification data and mood actuation data for a different occupant.

20. The media of claim 16, wherein the one or more scents dispersed are further associated with an additional mood actuation profile of an additional personalized occupant profile for an additional occupant of the vehicle.

* * * * *